United States Patent
Dugstad et al.

(10) Patent No.: US 9,347,922 B2
(45) Date of Patent: May 24, 2016

(54) METHOD AND APPARATUS FOR ANALYZING ALKALINITY CONDITIONS IN AQUEOUS LIQUIDS

(75) Inventors: Arne Dugstad, Oslo (NO); Marion Seiersten, Oslo (NO)

(73) Assignee: Institutt for Energiteknikk, Kjeller (NO)

( * ) Notice: Subject to any disclaimer, the term of this patent is extended or adjusted under 35 U.S.C. 154(b) by 186 days.

(21) Appl. No.: 14/116,895

(22) PCT Filed: May 11, 2012

(86) PCT No.: PCT/EP2012/058824
§ 371 (c)(1),
(2), (4) Date: Dec. 31, 2013

(87) PCT Pub. No.: WO2012/152935
PCT Pub. Date: Nov. 15, 2012

(65) Prior Publication Data
US 2014/0106464 A1  Apr. 17, 2014

(30) Foreign Application Priority Data
May 11, 2011  (NO) .................................. 20110705

(51) Int. Cl.
*G01N 31/16* (2006.01)
*G01N 31/00* (2006.01)
*G01N 33/18* (2006.01)

(52) U.S. Cl.
CPC ............... *G01N 31/16* (2013.01); *G01N 31/00* (2013.01); *G01N 33/18* (2013.01); *C02F 2209/07* (2013.01)

(58) Field of Classification Search
None
See application file for complete search history.

(56) References Cited

U.S. PATENT DOCUMENTS

| 4,277,343 A | 7/1981 | Paz |
| 5,747,342 A | 5/1998 | Zupanovich |
| 2006/0234389 A1* | 10/2006 | Byrne et al. ................. 436/163 |

FOREIGN PATENT DOCUMENTS

JP   2009264913 A   11/2009

OTHER PUBLICATIONS

Zhu Jianmin et al., Development of Total Alkalinity Grey Control System of Boiler Water, Journal of Grey System; 2006, vol. 18 Issue 2, p. 93.
International Search Report and Written Opinion dated Aug. 1, 2012 for International Application Serial No. PCT/EP2012/058824, International Filing Date: May 11, 2012 consisting of 15 pages.

* cited by examiner

*Primary Examiner* — Robert Xu
(74) *Attorney, Agent, or Firm* — Christopher & Weisberg, P.A.

(57) ABSTRACT

Method for analyzing the alkalinity conditions in aqueous liquids, comprising: sampling a known amount of the aqueous liquid and placing it in a container of known volume, measuring pH in the sampled liquid and pressure in the container, adding a known amount of $CO_2$ to the sampled liquid, and measuring pH in the sampled liquid and the pressure in the container, and finally calculating the total alkalinity based on the values from the performed measurements. An apparatus for conducting the method is also described as well as a method for controlling chemistry of a glycol containing liquid in a system for recovery of glycol.

8 Claims, 1 Drawing Sheet

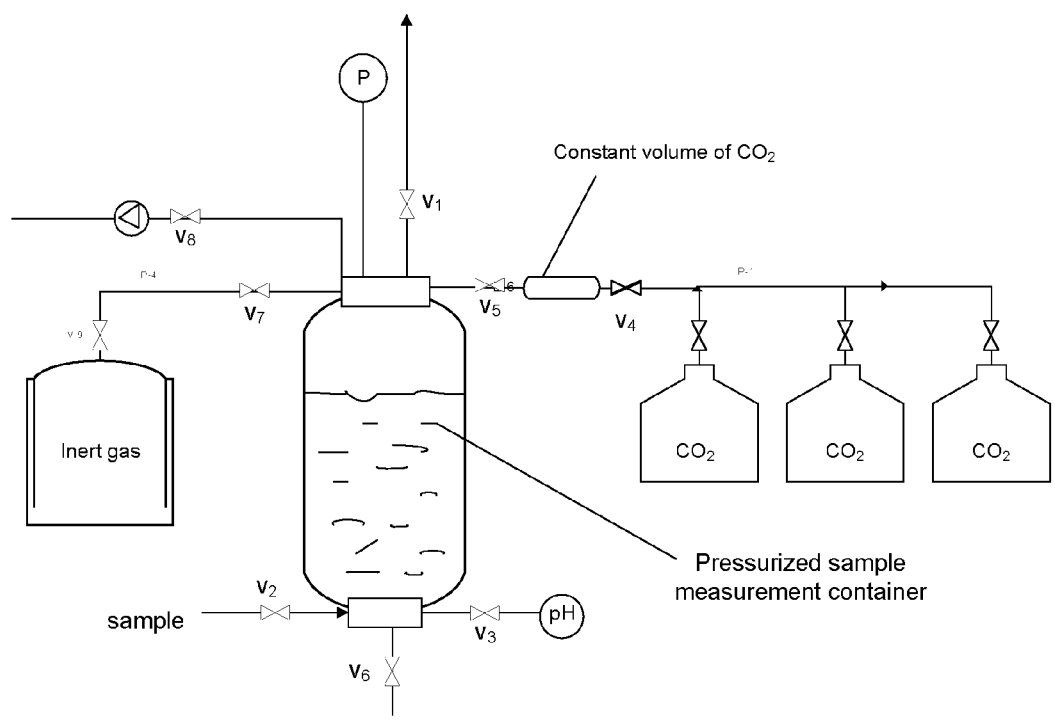

METHOD AND APPARATUS FOR ANALYZING ALKALINITY CONDITIONS IN AQUEOUS LIQUIDS

CROSS-REFERENCE TO RELATED APPLICATIONS

This application is a Submission Under 35 U.S.C. 371 for U.S. National Stage Patent Application of, and claims priority to, International Application Number PCT/EP2012/058824 entitled METHOD AND APPARATUS FOR ANALYZING ALKALINITY CONDITIONS IN AQUEOUS LIQUIDS, filed May 11, 2012, which is related to and claims priority to Norwegian Patent Number 20110705, filed May 11, 2011, the entirety of all of which are incorporated herein by reference.

The present invention concerns a method and apparatus for determining total alkalinity in aqueous solutions and more specifically its relative contribution by the components $OH^-$, $CO_3^{2-}$, and $HCO_3^{2-}$. A method for controlling chemistry of a glycol containing liquid in a system for recovery of glycol is also comprised.

BACKGROUND

In some connection it is important to control the alkalinity of aqueous solutions. This may be the case in chemical industrial processes where it is important to maintain alkalinity within certain limits to ensure desired reactivity or the opposite, e.g. to prevent corrosion or the like.

A specific and commercially important application is in relation to recovery of petroleum products, especially offshore, where mixtures of petroleum components, inevitably comprise some water, and in which circulation/recirculation of a glycol containing liquid is used for hydrate inhibition in the production system for gas and condensate. In such connections it is important to have control over alkalinity. This includes control of alkalinity in water-lean glycol injected into the production system and in the salt removal systems used for regeneration of water-rich glycol.

By glycol, we mean here the various forms of glycol compositions, mono-ethylene glycol (MEG) [ethane-1,2-diol], di-ethylene glycol (DEG) [2-hydroxyethoxy)ethan-2-ol], Tri-ethylene glycol (TEG) [2-[2-(2-Hydroxyethoxy)ethoxy]ethanol], and other Poly-ethylene glycols (PEG) as well as propylene glycol (PG) [1,2-propanediol]. However, precise measurement of alkalinity according to the invention provides valuable advantages for the use of a broader range of alcohol-based Thermodynamic Hydrate Inhibitors (THI), such as methanol and ethanol and also for purely aqueous solutions.

A discussion of glycol regeneration systems is given by C. A: Nazzer: "Advances in Glycol Reclamation Technology" (OTC 18010), presented at the 2006 Offshore Technology Conference, OTC, in Houston, Tex. USA, 1-4 May 2006.

Relevant background information in this technical field is also found in a publication of S. Brustad, K.-P. Løken, and J. G. Waalmann: "Hydrate Prevention using MEG instead of MeOH: Impact of experience from major Norwegian developments on technology selection for injection and recovery of MEG" (OTC 17355), presented at the OTC in Houston, Tex. USA 2-5 May, 2005.

An example of the importance of controlling the alkalinity of glycol applied for hydrate inhibition is given by O. Hagerup and S. Olsen: "Corrosion Control by pH stabilizer, Materials and Corrosion Monitoring in a 160 km Multiphase Offshore Pipeline", CORROSION/2003, Paper No.03328, NACE, Houston, 2003.

The commonly used principle for determining the condition of such solutions comprises isolating an amount of the solution to be controlled and titrate with acid and alternative method is to allow $CO_2$ to bubble through the solution until is it saturated therewith, whereafter pH is measured. A disadvantage with the first method is that it fails when the solution contains bases that are weaker than bicarbonate. A disadvantage with the second method is that the amount of $CO_2$ added is not known and the pH value measured therefore does not reveal all information of interest. In addition, bubbles generate foam in the solution, making measurements difficult. Any presence of salts of (weak) organic acids, which commonly occur, will interfere with the measurements based on titration.

Object

It is thus an object of the present invention to provide a method for determining alkalinity quickly and reliably in aqueous solutions, with high accuracy, using inexpensive means.

The Present Invention

The above mentioned objects are achieved by the present invention which according to a first aspect comprises a method as defined by the appended claim 1.

According to another aspect the invention comprises an apparatus for performing the method, said apparatus being disclosed by claim 10.

According to yet another aspect the present invention concerns a method related to controlling chemistry of glycol-containing-liquid in a system for recovery of glycol as defined by claim 14, said method comprising all steps in the method according to the first aspect of the invention.

Preferred embodiments of the inventions are disclosed by the dependent claims.

By "unbonded $CO_2$" as used herein is understood dissolved or dispersed $CO_2$ molecules in the liquid, i.e. not in the form of $HCO_3^-$ or $CO_3^{2-}$.

While alkalinity analysis is the technical field of this invention, it should be mentioned that a pH measurement in the acidic area (negative alkalinity) does not imply that the method is irrelevant or useless. It simply implies that alkaline addition is required to bring the pH of the liquid back to the desired pH before the method according to the present invention is continued.

It should be emphasized that the term "comprises/comprising" when used in this specification is taken to specify the presence of stated features, integers, steps or components, but does not preclude the presence or addition of one or more other features, integers, steps, components or groups thereof. In the following description, for purposes of explanation and not limitation, specific details are set forth such as particular architectures, interfaces, techniques, etc. in order to provide a thorough understanding of the invention. However, it will be apparent to those skilled in the art that the invention may be practiced in other embodiments that depart from these specific details. In other instances, detailed descriptions of well-known devices and methods are omitted so as not to obscure the description of the invention with unnecessary detail.

While the method according to the present invention may be carried out as a fully manual operation, the method may also be automatized and set to run at fixed or programmable intervals.

FIGURES

FIG. 1 is a schematic drawing of an apparatus for automatic performance of the method according to the present invention.

The present invention, providing a robust, precise and repeatable process is well adapted for automatisation. FIG. 1 illustrates schematically an embodiment of an automated analyzer of the present invention, and a possible rough automation sequence process will be described hereinafter with reference to FIG. 1.

The fluid being measured is typically under pressure, and separated from the analyzer by the valve V2. The fluid to be sampled is allowed in at V2, and fills up the measurement container up to 90% of the total volume of the container. Between two measurements, the container is typically filled with a gas not containing $CO_2$, such as nitrogen, which may have been blown through the measurement container at the end of the preceding measurement. Venting the pre-existing gas (nitrogen) may be done at V1 upon opening V2, or it may be done afterwards. For example in the case of a foaming sample, it may be an advantage not to vent at the beginning, let the sample in, let the foam be pressurized and settle for a time, then open V1 to obtain wished pressure. An alternative in the case of foam may be to connect V1 to a tube projecting further inside the measurement container so as first to let liquid out when opening V1. An alternative is also to fill up the measurement container thanks to vacuum, generated by a vacuum pump and transmitted by V8. Filling may be controlled by pressure, by a timer and/or by for example, filling level control sensors (represented here by a Level Switch High, LSH, and a Level Switch Low, LSL).

At that stage, one of the $CO_2$ removal operations can be performed: bubbling with a non-$CO_2$ containing gas, heating, resting, or applying vacuum.

Then, pressure and pH are measured. A fixed and known quantity of $CO_2$ gas is let in, for example by opening V5 after a calibrated buffer volume has been filled by $CO_2$ under pressure, preferably higher than the sample pressure. The calibrated volume is then refilled for next measurement thanks to the sequential control of valves V4 and V5. An alternative is to let CO2 in based on a timer controlling opening of an inlet valve. After $CO_2$ has been let in, a stirrer is run for typically several minutes.

A new set of measures of pressure P and pH is taken, and alkalinity characteristics derived. Then, the container is emptied and cleaned. For example, V2 is opened and under the pressure of gas, the container expels the liquid when opening V6, and an extra flushing or drying can be performed by flowing a liquid or a gas, for example an inert gas, through V7, blowing away the remaining drops of liquid out at V6. Finally, V6 is shut, then V7.

All sensors, valve actuators and controls are driven by a control system, based on a personal computer, a Programmable Logic Controller (PLC), or any other control system as known in the art.

Basis for the Calculations

Below the basic principles behind the calculations according to the present invention are discussed.

Total alkalinity is calculated on the basis of measured pH and measured $CO_2$ pressure according to the following equation:

$$\text{Total alkalinity} = K^* p_{CO2}/10^{-pH}, \qquad \text{I}$$

where K is a constant defined by ambient temperature, measured pressure and ion concentration in the aqueous solution, as well as the presence of other solvents, while $p_{CO2}$ is the difference between pressure in the container before and after $CO_2$ addition.

$$C_{CO_2,d} + C_{OH^-} + C_{CO_3^{2-}} = (mo_0 - mo_1)/V_V \qquad \text{II}$$

where $C_{CO_2,d}$ is the molar concentration of $CO_2$ dissolved in liquid, $C_{OH^-}$ is the molar concentration of $OH^-$ reacting with $CO_2$, $C_{CO_3^{2-}}$ is the molar concentration of $CO_3^{2-}$ reacting with $CO_2$, $mo_0$ is mole $CO_2$ added, $mo_1$ is mole $CO_2$ in the gas at equilibrium and $V_V$ is the sampled amount (volume) of liquid.

$C_{CO_2}^d$ is also defined by:

$$C_{CO_2}^d = p_{CO2} * K_H \qquad \text{III}$$

where $p_{CO2}$ is the $CO_2$ pressure measured in gas phase and $K_H$ is the solubility constant of $CO_2$.

When $$C_{OH^-} + C_{CO_3^{2-}} = (mo_0 - mo_1)/V_V - C_{CO_2,d} > 0 \qquad \text{IV}$$

which is always the case in situations of interest for the present invention, then $$\text{Total alkalinity} = C_{OH^-} + 2 * C_{CO_3^{2-}} \qquad \text{V}$$

Carbonate concentration is given by:

$$C_{CO_3^{2-}} = \text{Total alkalinity} - (mo_0 - mo_1)/V_V + C_{CO_2,d} \qquad \text{VI}$$

while $OH^-$ concentration is given by $$C_{OH^-} = \text{Total alkalinity} - 2 * C_{CO_3^{2-}} \qquad \text{VII}$$

These formulas allow an accurate calculation of total alkalinity as well as the components thereof when performing the present invention. It is preferred to frequently calibrate the basis for the calculations by determining the constant K and the solubility constant $K_H$ of $CO_2$ by addition of known amount of alkalinity.

In order to ensure that the sampled liquid does not contain $CO_2$ which is not chemically bonded, it is preferred to treat the sampled liquid in one or more of the following manners prior to conducting the measurements:

bubbling the sampled amount of the aqueous liquid with $N_2$ or other inert gases
heating the sampled amount of the aqueous liquid,
allowing the sampled amount of the aqueous liquid to rest before continuing, and
applying vacuum to the sampled amount of the aqueous liquid.

For the purpose of said treatment, the apparatus should preferably be equipped with suitable means therefore.

By "inert gas" as used in this context is contemplated any gas not interfering with the measurements, typically $N_2$, while principally any gas not containing $CO_2$ could be used as inert gas.

In order to obtain reliable measurements, the amount of liquid sampled should not exceed 90% of the container volume and neither constitute less than 10% of the container volume.

To ensure that the $CO_2$ added in step iii is present in gaseous form only, the pressure should be maintained at a level no higher than 55 bar while a pressure in the range between 3 and 10 bar is preferred. Reducing the pressure under 3 bar may result in less precise measurements while increasing the pressure above 10 bar will require inconveniently expensive equipment.

All measurements required by the method according to the present invention may be performed by standard equipment therefore.

The apparatus should preferably be approved for a pressure of at least 3 bar and more preferably at least 10 bar to allow versatility of use.

For the purpose of its calibration, the apparatus should preferably comprise means for adding defined quantities of alkalinity or acid with known concentration.

Whereas current glycol reclamation plant engineering allows for a full container skid to host alkalinity analysis, an analyzer according to the present invention would fit in a portable box. This enables a more flexible use by operators, and reduces volume required and costs.

EXAMPLE

The following is a conceptual example of conducting the method according to the present invention in an industrial real life application in which alkalinity is determined in e.g. a water lean glycol.

Total volume, measurement vessel with all attachments: 700 ml
Added liquid: 500 ml
Gas volume: 200 ml
Added $CO_2$ ($mo_0$): 8 g (0.189 mol)
Initial pH in liquid: 12.01
Initial pressure: 1.01 bar
After $CO_2$ addition:
pH: 5.33
Pressure: 7.69 bar; $CO_2$ partial pressure ($pCO_2$): 6.68 bar
K at 20° C. is $2.23*10^{-8}$
This gives a total alkalinity=$K*p_{CO2}/10^{-pH}=2.23*10^{-8}*6.68/10^{-5.33}=0.032M$ Concentration of dissolved $CO_2$ in the liquid volume is: $C_{CO_2,d}=p_{CO2}*K_H=0.233$ when $K_H=0.0349$ Number of mole $CO_2$ in the gas phase at equilibrium ($mo_1$): ($CO_2$ partial pressure (bar) times volume (L) divided by gas constant (0.08314 L·bar·$K^{-1}$·$mol^{-1}$) divided by temperature (K): 6.68*0.2/0.08314/293.15) mol=0.055 mol.

Carbonate concentration is:

$C_{CO_3}^{2-}$=Total alkalinity−$(mo_0-mo_1)/V_V+C_{CO_2,d}=$
(0.032 −(0.189−0.055)/0.5+0.233)M=0.011M Hydroxide concentration is: $C_{OH}^-$=Total alkalinity−$2*C_{CO_3}^{2-}$=0.032M−2*0.011M=0.010M The present invention as discussed above thus fulfills the above mentioned objects and provides a method and an apparatus offering a highly improved control of the alkalinity conditions in aqueous liquids irrespective of application.

It is worth noticing that improved measurements and analysis will lead to reduced use of chemicals and reduced problems in the form of corrosion and scaling, or the "balance" between these problems.

The invention claimed is:

1. A method for analyzing the alkalinity conditions in aqueous liquids, the method comprising:

I. sampling a known amount of the aqueous liquid and placing it in a container of known volume;
II. measuring pH in the sampled liquid and the pressure in the container;
III. adding a known amount of $CO_2$ to the container; and
IV. measuring pH in the sampled liquid and the pressure in the container; and
V. calculating total alkalinity,
wherein total alkalinity is calculated on the basis of measured pH and measured $CO_2$ pressure according to the following equation:

Total alkalinity =$K*p_{CO2}/10^{-pH}$, where K is a constant defined by ambient temperature, measured pressure and ion concentration in the aqueous solution and the presence and concentration of other solvents, while pco2 is the difference between pressure in the container before and after $CO_2$ addition.

2. The method as claimed in claim 1, further comprising under step V also calculating the concentration of components $OH^-$, $CO_3^{2-}$ and $HCO_3^-$ based on the values from the measurements performed in II and IV.

3. The method as claimed in claim 1, further comprising under step III allowing the container to equilibrate before proceeding to step IV.

4. The method as claimed in claim 1, further comprising an additional step prior to step II, in order to eliminate any unbonded $CO_2$ in the solution by performing at least one the following:
bubbling the sample of aqueous liquid with $N_2$, or other inert gases;
heating the sampled sample of aqueous liquid;
allowing the sample of aqueous liquid to rest before continuing; and
applying vacuum to the sample of aqueous liquid.

5. The method as claimed in claim 1, wherein the amount of liquid sampled fills between 10% and 90% of the container volume.

6. The method as claimed in claim 1, wherein the $CO_3^2$ -concentration is calculated as:

$C_{CO_3}^{2-}=^{Total}$ alkalinity −$(mo_0-mo_1)/V_V+C_{CO2,d}$ where $V_V$ is the volume of liquid sampled and $C_{CO2,d}$ is the molar concentration of $CO_2$ in the liquid, provided that: $C_{OH}^-+C_{CO3}^{2-}=(mo_0-mo_1)/V_V-C_{CO2,d}>0$.

7. The method as claimed in claim 6, wherein the $OH^-$ concentration is calculated as:

$C_{OH}^-$=Total alkalinity −2 $*C_{CO3}^{2-}$.

8. The method as claimed in claim 1, wherein the basis for the calculations is calibrated by determining the constant K and the solubility constant $K_H$ of $CO_2$ by addition of known amount of alkalinity.

* * * * *